United States Patent
Taktak et al.

(10) Patent No.: US 10,126,314 B2
(45) Date of Patent: *Nov. 13, 2018

(54) NMR DETECTION OF COAGULATION TIME

(71) Applicant: T2 Biosystems, Inc., Lexington, MA (US)

(72) Inventors: Sonia Taktak, Cambridge, MA (US); Brian M. Mozeleski, Knox, ME (US); Thomas J. Lowery, Jr., Belmont, MA (US)

(73) Assignee: T2 Biosystems, Inc., Lexington, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/842,388

(22) Filed: Sep. 1, 2015

(65) Prior Publication Data

US 2015/0369829 A1     Dec. 24, 2015

Related U.S. Application Data

(63) Continuation of application No. 13/124,318, filed as application No. PCT/US2009/062537 on Oct. 29, 2009, now Pat. No. 9,157,974.

(60) Provisional application No. 61/109,367, filed on Oct. 29, 2008.

(51) Int. Cl.
| | |
|---|---|
| G01N 33/86 | (2006.01) |
| G01N 24/08 | (2006.01) |
| C12Q 1/56 | (2006.01) |
| G01N 33/49 | (2006.01) |
| G01R 33/465 | (2006.01) |
| G01R 33/50 | (2006.01) |
| G01R 33/561 | (2006.01) |
| G01N 33/483 | (2006.01) |
| G01N 33/487 | (2006.01) |
| G01N 33/48 | (2006.01) |

(52) U.S. Cl.
CPC ............ *G01N 33/86* (2013.01); *C12Q 1/56* (2013.01); *G01N 24/088* (2013.01); *G01N 33/4905* (2013.01); *G01R 33/465* (2013.01); *G01R 33/50* (2013.01); *G01R 33/5617* (2013.01); *G01N 33/48* (2013.01); *G01N 33/483* (2013.01); *G01N 33/487* (2013.01)

(58) Field of Classification Search
CPC .. G01R 33/5617; G01R 33/465; G01R 33/50; G01N 33/48; G01N 33/483; G01N 33/487; G01N 33/49; G01N 33/4905; G01N 33/86
See application file for complete search history.

(56) References Cited

U.S. PATENT DOCUMENTS

| | | | |
|---|---|---|---|
| 4,101,435 | A | 7/1978 | Hasegawa et al. |
| 4,374,360 | A | 2/1983 | Sepponen |
| 4,452,773 | A | 6/1984 | Molday |
| 4,875,486 | A | 10/1989 | Rapoport et al. |
| 4,920,061 | A | 4/1990 | Poynton et al. |
| 5,042,488 | A | 8/1991 | Ackerman |
| 5,049,819 | A | 9/1991 | Dechene et al. |
| 5,136,095 | A | 8/1992 | Tarnowski et al. |
| 5,164,297 | A | 11/1992 | Josephson et al. |
| 5,204,457 | A | 4/1993 | Maruno et al. |
| 5,254,460 | A | 10/1993 | Josephson et al. |
| 5,262,176 | A | 11/1993 | Palmacci et al. |
| 5,424,419 | A | 6/1995 | Hasegawa et al. |
| 5,445,970 | A | 8/1995 | Rohr |
| 5,445,971 | A | 8/1995 | Rohr |
| 5,492,814 | A | 2/1996 | Weissleder |
| 5,637,469 | A | 6/1997 | Wilding et al. |
| 5,801,003 | A | 9/1998 | Shimamura et al. |
| 6,013,188 | A | 1/2000 | Terstappen et al. |
| 6,165,378 | A | 12/2000 | Maruno et al. |
| 6,294,342 | B1 | 9/2001 | Rohr et al. |
| 6,297,062 | B1 | 10/2001 | Gombinski |
| 6,307,372 | B1 | 10/2001 | Sugarman et al. |
| 6,342,396 | B1 | 1/2002 | Perrin et al. |
| 6,361,944 | B1 | 3/2002 | Mirkin et al. |
| 6,500,343 | B2 | 12/2002 | Siddiqi |
| 6,548,311 | B1 | 4/2003 | Knoll |
| 6,599,498 | B1 | 7/2003 | Groman et al. |
| 6,630,355 | B1 | 10/2003 | Pivarnik et al. |
| 6,767,635 | B1 | 7/2004 | Bahr et al. |
| 6,866,838 | B1 | 3/2005 | Mondain-Monval et al. |

(Continued)

FOREIGN PATENT DOCUMENTS

| | | |
|---|---|---|
| EP | 1669761 A2 | 6/2006 |
| JP | 2000-166897 A | 6/2000 |

(Continued)

OTHER PUBLICATIONS

Millot, Y. "CPMG pulse program with HADC digitizer and digital filtering for AVANCE AQX spectrometer." Obtained from <http://http://web.archive.org/web/20060313160020/http://www.pascal-man.com/pulseprogram/cpmg-HADC-AQX.shtml> on Mar. 17, 2017. Archived on Mar. 13, 2006.*
"Anti-Clotting Agents Explained," <http://www.strokeassociation.org/STROKEORG/LifeAfterStroke/HealthyLivingAfterStroke/ManagingMedicines/Anti-Clotting-Agents-Explained_UCM_310452_Article.jsp#.Vo6FzmfSmig>, retrieved on Jan. 7, 2016 (2 pages).
Atanasijevic et al., "Calcium-sensitive MRI contrast agents based on superparamagnetic iron oxide nanoparticles and calmodulin." Proc Natl Acad Sci USA. 103(40):14707-12 (2006).

(Continued)

*Primary Examiner* — Christopher Adam Hixson
(74) *Attorney, Agent, or Firm* — Clark & Elbing LLP

(57) ABSTRACT

The invention relates to detecting coagulation and coagulation-related activities including agglutination and fibrinolysis of samples. More particularly the invention relates to methods and apparatus for monitoring coagulation and/or obtaining a coagulation time of a sample using NMR-based detectors.

19 Claims, 7 Drawing Sheets

(56) References Cited

U.S. PATENT DOCUMENTS

| | | | |
|---|---|---|---|
| 6,884,357 | B2 | 4/2005 | Siddiqi |
| 6,940,378 | B2 | 9/2005 | Miller et al. |
| 7,001,589 | B2 | 2/2006 | Mondain-Monval et al. |
| 7,018,849 | B2 | 3/2006 | Piasio et al. |
| 7,179,652 | B2 | 2/2007 | Cohen et al. |
| 7,217,457 | B2 | 5/2007 | Elaissari et al. |
| 7,217,542 | B2 | 5/2007 | Tyvoll et al. |
| 7,274,191 | B2 | 9/2007 | Park et al. |
| 7,332,353 | B2 | 2/2008 | Baudry et al. |
| 7,517,457 | B2 | 4/2009 | Siddiqi |
| 7,553,542 | B2 | 6/2009 | Ou et al. |
| 7,564,245 | B2 | 7/2009 | Lee |
| 7,781,228 | B2 | 8/2010 | Menon et al. |
| 7,829,350 | B2 | 11/2010 | Josephson et al. |
| 8,339,135 | B2 | 12/2012 | Sillerud et al. |
| 9,157,974 | B2 * | 10/2015 | Taktak .............. G01R 33/465 |
| 9,599,627 | B2 | 3/2017 | Lowery, Jr. et al. |
| 2002/0102214 | A1 | 8/2002 | Briley-Saebo et al. |
| 2003/0054432 | A1 | 3/2003 | Chen et al. |
| 2003/0216638 | A1 | 11/2003 | Dharmakumar et al. |
| 2003/0219904 | A1 | 11/2003 | Cohen et al. |
| 2003/0222648 | A1 | 12/2003 | Fan |
| 2004/0175388 | A1 | 9/2004 | Ding et al. |
| 2004/0214348 | A1 | 10/2004 | Nicholson et al. |
| 2006/0121617 | A1 | 6/2006 | Henckel et al. |
| 2006/0269965 | A1 | 11/2006 | Josephson et al. |
| 2007/0038121 | A1 | 2/2007 | Feldman et al. |
| 2007/0116602 | A1 | 5/2007 | Lee |
| 2007/0166730 | A1 | 7/2007 | Menon et al. |
| 2008/0199539 | A1 | 8/2008 | Baker et al. |
| 2008/0204022 | A1 | 8/2008 | Sillerud et al. |
| 2008/0261261 | A1 | 10/2008 | Grimes et al. |
| 2008/0305048 | A1 | 12/2008 | Josephson et al. |
| 2009/0099342 | A1 | 4/2009 | Braconnot et al. |
| 2010/0039109 | A1 | 2/2010 | Cheng et al. |
| 2010/0051362 | A1 | 3/2010 | Ren et al. |
| 2010/0072994 | A1 | 3/2010 | Lee et al. |
| 2010/0120174 | A1 | 5/2010 | Josephson et al. |
| 2011/0312002 | A1 | 12/2011 | Taktak et al. |
| 2012/0100546 | A1 | 4/2012 | Lowery, Jr. et al. |
| 2013/0244238 | A1 | 9/2013 | Neely et al. |
| 2013/0260367 | A1 | 10/2013 | Lowery, Jr. et al. |
| 2014/0212901 | A1 | 7/2014 | Lowery, Jr. et al. |
| 2016/0018421 | A1 | 1/2016 | Lowery, Jr. et al. |

FOREIGN PATENT DOCUMENTS

| | | |
|---|---|---|
| JP | 2006-162623 A | 6/2006 |
| JP | 3876022 B2 | 1/2007 |
| JP | 3917239 B2 | 5/2007 |
| JP | 2008128883 A | 6/2008 |
| JP | 2008209350 A | 9/2008 |
| WO | WO-90/06045 A2 | 6/1990 |
| WO | WO-91/17428 A1 | 11/1991 |
| WO | WO-97/40181 A1 | 10/1997 |
| WO | WO-98/04740 A1 | 2/1998 |
| WO | WO-01/00876 A1 | 1/2001 |
| WO | WO-01/11360 A2 | 2/2001 |
| WO | WO-01/19405 A2 | 3/2001 |
| WO | WO-02/098364 A2 | 12/2002 |
| WO | WO-2005/099419 A2 | 10/2005 |
| WO | WO-2005/111596 A1 | 11/2005 |
| WO | WO-2008/007270 A2 | 1/2008 |
| WO | WO-2008/010111 A2 | 1/2008 |
| WO | WO-2008/072156 A2 | 6/2008 |
| WO | WO-2008/119054 A1 | 10/2008 |
| WO | WO-2008/137721 A2 | 11/2008 |
| WO | WO-2009/017697 A2 | 2/2009 |
| WO | WO-2009/026251 A1 | 2/2009 |
| WO | WO-2009/045354 A1 | 4/2009 |
| WO | WO-2009/045551 A1 | 4/2009 |
| WO | WO-2009/055587 A1 | 4/2009 |
| WO | WO-2009/061481 A1 | 5/2009 |
| WO | WO-2009/085214 A1 | 7/2009 |
| WO | WO-2010/002479 A1 | 1/2010 |
| WO | WO-2010/051362 A1 | 5/2010 |
| WO | WO-2013/010080 A1 | 1/2013 |
| WO | WO-2013/043858 A1 | 3/2013 |
| WO | WO-2013/190071 A2 | 12/2013 |
| WO | WO-2014/004573 A1 | 1/2014 |

OTHER PUBLICATIONS

Azoury et al., "Structural changes in fibrin clot associated with the proteolytic activity induced by tissue type plasminogen activator. An NMR study," Biochim Biophys Acta. 295(3):295-300 (1989).

Baudry et al., "Acceleration of the recognition rate between grafted ligands and receptors with magnetic forces." Proc Natl Acad Sci U.S.A. 103(44):16076-8 (2006).

Blackmore et al., "Magnetic resonance imaging of blood and clots in vitro." Invest Radiol. 25(12):1316-24 (1990).

Blinc et al., "Proton NMR study of the state of water in fibrin gels, plasma, and blood clots," Magn Reson Med. 14(1):105-22 (1990).

Brooks et al., "Nuclear magnetic relaxation in blood." IEEE Trans Biomed Eng. 22(1):12-18 (1975).

Bryant et al., "Magnetic relaxation in blood and blood clots." Magn Reson Med. 13(1):133-44 (1990).

Carr, "Development of platelet contractile force as a research and clinical measure of platelet function." Cell Biochem Biophys. 38(1):55-78 (2003).

Cazenave et al., "Preparation of washed platelet suspensions from human and rodent blood," Methods Mol Biol. 272(1):13-28 (2004).

Chan et al., "Reference values for kaolin-activated thromboelastography in healthy children." Anesth Analg. 105(6):1610-3 (2007).

Clark et al., "Acute hematomas: Effects of deoxygenation, hematocrit, and fibrin-clot formation and retraction on T2 shortening," Radiology. 175(1):201-6 (1990).

Cohen-Tannoudji et al., "Measuring the kinetics of biomolecular recognition with magnetic colloids." Phys Rev Lett. 100(10):108301-1-4 (2008).

Colombo et al., "Femtomolar detection of autoantibodies by magnetic relaxation nanosensors." Anal Biochem. 392(1):96-102 (2009).

Costanzo et al., "Protein-ligand mediated aggregation of nanoparticles: a study of synthesis and assembly mechanism," Chem Mater. 16:1775-1785 (2004).

Cover, "A robust and reliable method for detecting signals of interest in multiexponential decays," Rev Sci Instrum. 79(5):055106 1-11 (2008).

Craft et al., "A novel modification of the thrombelastograph assay, isolating platelet function, correlates with optical platelet aggregation." J Lab Clin Med. 143(5):301-9 (2004).

De Gaetano et al., "Effect of platelets on clot structuration, a thrombelastographic study." Thromb Res. 3:425-35 (1973).

De Gaetano et al., "Retraction of reptilase-clots in the presence of agents inducing or inhibiting the platelet adhesion-aggregation reaction." Thromb Resear. 2(1):71-84 (1973).

Demas et al., "Portable, low-cost NMR with laser-lathe lithography produced microcoils." J Magn Reson. 189(1):1-20 (2007).

Downey et al., "Novel and diagnostically applicable information from optical waveform analysis of bood coagulation in disseminated intravascular coagulation." Br J Haematol. 98(1):68-73 (1997).

Dreyfus et al., "Microscopic artificial swimmers." Nature. 437(7060):862-5 (2005).

Edzes, "An analysis of the use of pulse multiplets in the single scan determination of spin-lattice relaxation rates." J Magne Reson. 17:301-13 (1975).

Enriquez et al., "Point-of-care coagulation testing and transfusion algorithms." Br J Anaesthe. 103:i14-i22 (2009).

Examination Report for Australian Application No. 2009308841, dated Jun. 24, 2013 (3 pages).

Extended European Search Report for European Application No. 12812054.0, dated Feb. 23, 2015 (10 pages).

Extended European Search Report for European Patent Application No. 12833431.5, dated May 4, 2015 (5 pages).

Extended European Search Report for European Patent Application No. 09824124.3, dated Dec. 4, 2013 (13 pages).

(56) References Cited

OTHER PUBLICATIONS

Fry et al., "A new approach to template purification for sequencing applications using paramagnetic particles." Biotechniques. 13(1):124-6, 128-31 (1992).
Gijs, "Magnetic bead handling on-chip: new opportunities for analytical applications." Microfluid Nanofluid. 1:22-40 (2004).
Gillis et al., "Transverse relaxation of solvent protons induced by magnetized spheres: application to ferritin, erythrocytes, and magnetite." Magn Reson Med. 5(4):323-45 (1987).
Gomori et al., "NMR relaxation times of blood: dependence on field strength, oxidation state, and cell integrity." J Comp Assist Tomog. 11(4):684-90 (1987).
Grimm et al., "Novel nanosensors for rapid analysis of telomerase activity." Cancer Res. 64(2):639-43 (2004).
Hansen et al., "Effect of gel firmness at cutting time, pH, and temperature on rennet coagulation and syneresis: An in situ 1H NMR relaxation study." J Agric Food Chem. 58(1):513-9 (2010).
Herbst et al., "A review of water diffusion measurement by NMR in human red blood cells." Am J Physiol. 256(5 Pt 1):C1097-104 (1989).
Hiltbrand et al., "Variations in proton relaxation in the weak field during coagulation." C. R. Acad Sci. II:1465-7 (1981).
Hong et al., "Magnetic microparticle aggregation for viscosity determination by magnetic resonance," Magn Reson Med. 59(3):515-20 (2008) (14 pages).
International Preliminary Report on Patentability and Written Opinion for International Patent Application No. PCT/US2012/046669, dated Jan. 23, 2014 (10 pages).
International Preliminary Report on Patentability for International Application No. PCT/US09/62537, dated Jul. 20, 2011 (16 pages).
International Preliminary Report on Patentability for International Patent Application No. PCT/US2012/056312, dated Mar. 25, 2014 (7 pages).
International Search Report and Written Opinion for International Application No. PCT/US2015/027784, dated Jul. 27, 2015 (12 pages).
International Search Report and Written Opinion for International Patent Application No. PCT/US13/73395, dated Mar. 27, 2014 (16 pages).
International Search Report for International Application No. PCT/US09/62537, dated Dec. 23, 2009 (3 pages).
International Search Report for International Application No. PCT/US12/46669 dated Oct. 26, 2012 (2 pages).
Istratov et al., "Exponential analysis in physical phenomena." Rev Sci Instrum. 70(2):1233-57 (1999).
Josephson et al., "High-efficiency intracellular magnetic labeling with novel superparamagnetic-Tat peptide conjugates." Bioconjug Chem. 10(2):186-191 (1999).
Josephson et al., "Magnetic nanosensors for the detection of oligonucleotide sequences." Angew Chem. 40(17):3204-6 (2001).
Kim et al., "Magnetic relaxation switch detection of human chorionic gonadotrophin." Bioconjug Chem. 18(6):2024-8 (2007).
Koenig et al., "Theory of 1/T1 and 1/T2 NMRD profiles of solutions of magnetic nanoparticles," Magn Reson Med. 34(2):227-33 (1995).
Koh et al., "Magnetic nanoparticle sensors." Sensors. 9(10):8130-45 (2009).
Koh et al., "Nanoparticle-target interactions parallel antibody-protein interactions." Anal Chem. 81(9):3618-22 (2009).
Koh et al., "Sensitive NMR sensors detect antibodies to influenza," Angew Chem Int Ed Engl. 47(22):4119-21 (2008) (8 pages).
Kriz et al., "Advancements toward magneto immunoassays." Biosens Bioelectron. 13(7-8):817-23 (1998).
Kriz et al., "Magnetic permeability measurements in bioanalysis and biosensors." Anal Chem. 68(11):1966-70 (1996).
Kroll, "Thromboelastography: theory and practice in measuring hemostasis." Clin Lab News. 8-10 (2010).
Kötitz et al., "Determination of the binding reaction between avidin and biotin by relaxation measurements of magnetic nanoparticles." J Magn Magn Mater. 194:62-8 (1999).
Landler et al., "In vitro T1- and T2-relaxation times of coagulating blood and thrombuses." Z Naturforsch C. 42(9-10):1135-9 (1987) (English Abstract Only).
Lee et al., "Ligand-receptor interactions in chains of colloids: when reactions are limited by rotational diffusion." Langmuir. 24(4):1296-307 (2008).
Lee et al., "Microelectromagnets for the control of magnetic nanoparticles." Appl Phys Letters. 79(20):3308-10 (2001).
Lewin et al., "Tat peptide-derivatized magnetic nanoparticles allow in vivo tracking and recovery of progenitor cells." Nat Biotechnol. 18(4):410-4 (2000).
Li, Yijia, Thesis: "Determining NMR relaxation times for porous media: Theory, measurement and the inverse problem," Master of Mathematics in Applied Mathematics, University of Waterloo, 2007 (147 pages).
Liu, "CMOS Magnetic Cell Manipulator and CMOS NMR Biomolecular Sensor," Harvard University Ph.D. dissertation, Nov. 5, 2007 (167 pages).
Lowery, Nanomaterials-Based Magnetic Relaxation Biosensors. *Nanomaterials for the Life Sciences vol. 4: Magnetic Nanomaterials*. Challa S. S. R. Kumar, 3-53 (2009).
Makiranta et al., "Master of Science Thesis," Tampere University of Technology, Oct. 2004 (English Abstract Included) (111 pages).
Makiranta et al., "Modeling and simulation of magnetic nanoparticle sensor", Proceedings of the 2005 IEEE, Shanghai, China, Sep. 1-4, 2005, 1256-59 (2005).
Malba et al., "Laser-lathe lithography—a novel method for manufacturing nuclear magnetic resonance microcoils." Biomed Micro. 5(1):21-7 (2003).
Martin et al., "Strong intrinsic mixing in vortex magnetic fields." Phys Rev E Stat Nonlin Soft Matter Phys. 80(1 Pt 2):016312 (2009) (6 pages).
Martin, "Theory of strong intrinsic mixing of particle suspensions in vortex magnetic fields." Phys Rev E State Nonlin Soft Matter Phys. 79(1 Pt 1):011503 (2009) (12 pages).
Massicotte et al., "Home monitoring of warfarin therapy in children with a whole blood prothrombin time monitor," J Pediatr. 127(3):389-94 (1995).
Massin et al., "Planar microcoil-based magnetic resonance imaging of cells", Transducers, Solid-state Sensors, Actuators and Microsystems 12th Int'l conference, Boston, Jun. 8-12, 2003, 967-970.
Massin et al., "Planar microcoil-based microfluidic NMR probes." J Mag Reson. 164(2):242-55 (2003).
Molday et al., "Immunospecific ferromagnetic iron-dextran reagents for the labeling and magnetic separation of cells." J Immuno Methods. 52(3):353-67 (1982).
Moser et al., "On-chip immune-agglutination assay with analyte capture by dynamic manipulation of superparamagnetic beads." Lab Chip. 9(22):3261-7 (2009).
Niemeyer et al., "Self-assembly of DNA-streptavidin nanostructures and their use as reagents in immuno-PCR." Nucleic Acid Res. 27(23):4553-61 (1999).
Notice of Reasons for Rejection for Japanese Patent Application No. 2011-534756, dated Apr. 2, 2013 (10 pages) (English Language Translation Included).
Notice of Reasons for Rejection for Japanese Patent Application No. 2011-534756, dated Jun. 10, 2014 (3 pages) (English Language Translation Included).
Notice of Reasons for Rejection for Japanese Patent Application No. 2011-534756, dated Oct. 29, 2013 (10 pages) (English Language Translation Included).
Nummi et al., "Effect of hemolysis and clotting on proton relaxation times of blood." Acta Radiolog Diag. 27(2): 225-30 (1986).
Office Action for Chinese Application No. 201280044411.X, dated Jan. 6, 2015 (22 pages).
Pell et al., "Optimized clinical T2 relaxometry with a standard CPMG sequence," J Magn Reson Imaging. 23(2):248-52 (2006).
Perez et al., "Magnetic relaxation switches capable of sensing molecular interactions." Nature Biotechnol. 20(8): 816-20 (2002).
Perez et al., "DNA-based magnetic nanoparticle assembly acts as a magnetic relaxation nanoswitch allowing screening of DNA-cleaving agents." J Am Chem Soc. 124(12):2856-7 (2002).

(56) References Cited

OTHER PUBLICATIONS

Perez et al., "Use of magnetic nanoparticles as nanosensors to probe for molecular interactions." Chembiochem. 5(3):261-4 (2004).
Perez et al., "Viral-induced self assembly of magnetic nanoparticles allows the detection of viral particles in biological media." J Am Chem Soc. 125(34):10192-3 (2003).
Schuhmacher et al., "NMR relaxation times T1 and T2 of water in plasma from patients with lung carcinoma: correlation of T2 with blood sedimentation rate," Magn Reson Med. 5(6):537-47 (1987).
Sezginer et al., "Very rapid simultaneous measurement of nuclear magnetic resonance spin-lattice relaxation time and spin-spin relaxation time." J Magn Reson. 92:504-27 (1991).
Shapiro et al., "Dynamic imaging with MRI contrast agents: quantitative considerations," Magn Reson Imaging. 24(4):449-462 (2006).
Sillerud et al., "1 H NMR detection of superparamagnetic nanoparticles at 1 T using a microcoil and novel tuning circuit." J Magn Reson. 181(2):181-90 (2006).
Spero et al., "Nanoparticle diffusion measures bulk clot permeability." Biophysical J. 101(4):943-50 (2011) (8 pages).
Stuhlmuller et al., "Effect of varying fibrinogen and hematocrit concentrations on magnetic resonance relaxation times of thrombus." Invest Radiol. 27(5):341-5 (1992).
Stuhlmuller et al., "Magnetic resonance characterization of blood coagulation in vitro." Invest Radiol. 26(4):343-7 (1991).
Sun et al., "Experimental study on T2 relaxation time or protons in water suspensions of iron-oxide nanoparticles: waiting time dependence," J Magn Magn Mater. 321(18):2971-5 (2009).
Syms et al., "MEMS Helmholtz coils for magnetic resonance imaging."J Micromec Microeng. 15(7):S1-9 (2005).
Tellier et al., "Evolution of water proton nuclear magnetic relaxation during milk coagulation and syneresis: structural implications." J Agric Food Chem. 41:2259-66 (1993).
Teyssier et al., "Résonance magnétique—dynamique de la coagulation du sang humain étudiée par dispersion des temps de la relaxation protonique/Magentic resonance—coagulation process for human blood studied by protonic relaxation time dispersion," Comptes Rendus de l'Acad. des Sciences. 299(8):395-8 (1984).
Thulborn et al., "Oxygenation dependence of the transverse relaxation time of water protons in whole blood at high field." Biochim Biophys Acta. 714(2):265-70 (1982).
Tong et al., "Coating optimization of superparamagnetic iron oxide nanoparticles for high T2 relaxivity." Nano Lett. 10(11):4607-13 (2010).
Tsourkas et al., "Magnetic relaxation switch immunosensors detect enantiomeric impurities." Angew Chem Int Ed Engl. 43(18):2395-9 (2004).
Vidmar et al., "A comparison of the ADC and T2 mapping in an assessment of blood-clot lysability." NMR Biomed. 23(1):34-40 (2009).
Vidmar et al., "An MRI study of the differences in the rate of thrombolysis between red blood cell-rich and platelet-rich components of venous thrombi ex vivo," J Magn Reson Imaging. 34(5):1184-91 (2011).
Vidmar et al., "Discrimination between red blood cell and platelet components of blood clots by MR microscopy." Eur Biophys J. 37(7):1235-40 (2008).
Weissleder et al., "Cell-specific targeting of nanoparticles by multivalent attachment of small molecules." Nat Biotechnol. 23(11):1418-23 (2005).
Written Opinion for International Application No. PCT/US09/62537, dated Dec. 23, 2009 (7 pages).
Wu et al., "1H-NMR spectroscopy on the nanoliter scale for static and on-line measurements." Anal Chem. 66(22):3849-57 (1994).
Cines et al., "Clot contraction: compression of erythrocytes into tightly packed polyhedra and redistribution of platelets and fibrin," Blood. 123(10):1596-603 (2014).
Examination Report for Australian Application No. 2012281017, dated Jul. 7, 2016 (3 pages).
Extended European Search Report for European Application No. 13860819.5, dated Jun. 30, 2016 (8 pages).
International Preliminary Report on Patentability for International Application No. PCT/US2015/027784, dated Nov. 1, 2016 (7 pages).
Skewis et al., "T2 magnetic resonance: a diagnostic platform for studying integrated hemostasis in whole blood—proof of concept," Clin Chem. 60(9):1174-82 (2014).
International Search Report and Written Opinion for International Application No. PCT/US16/39611, dated Sep. 22, 2016 (20 pages).
International Preliminary Report on Patentability for International Application No. PCT/US2016/039611, dated Dec. 26, 2017 (10 pages).
Extended European Search Report for European Application No. 17001484.9, dated Jan. 31, 2018 (8 pages).
Tsuji et al., "Limulus amoebocyte lysate assay for detection and quantitation of endotoxin in a small-volume parenteral product," Appl Environ Microbiol. 40(3):533-8 (1980).

\* cited by examiner

NMR DETECTION OF COAGULATION TIME

The invention relates to detecting coagulation and coagulation-related activities such as, for example, agglutination and fibrinolysis of samples (e.g., human blood samples). More particularly, the invention relates to methods and apparatus for obtaining a coagulation time of a sample (e.g., plasma, blood concentrate, citrated blood) using NMR-based detectors.

BACKGROUND OF THE INVENTION

Hemostasis, the physiological process of preventing excess blood loss by arresting flow via the formation of a hemostatic plug while maintaining blood in a fluid state within intact blood vessels, is maintained by tightly regulated interactions of the blood vessel wall, blood platelets, and blood plasma proteins. Under normal conditions there is a delicate balance between the individual components of the hemostatic system. Any disturbances in this balance, called the hemostatic potential, can result in either uncontrolled bleeding or formation of unwanted blood clots (thrombosis). Clinical assessment of clotting function has long been recognized to be important in management of surgical patients. Preoperatively, assessment of clotting function of a patient's blood is utilized as a predictor of risk of patient bleeding, allowing advanced preparation of blood components. Perioperative monitoring of clotting function of a patient's blood is also important because coagulopathies can be induced by hemodilution of procoagulants, fibrinogen and platelets, as a result of consumption of coagulation factors during surgical procedures, or cardiac procedures (e.g., cardiopulmonary bypass). Post-operative assessment of clotting function can also be crucial to a patient's successful recovery.

Coagulation is defined as transformation of a liquid or solution into a soft, semi-solid or solid mass. Blood naturally coagulates or clots to form a barrier when trauma or pathologic conditions cause vessel damage. There are two well-recognized coagulation pathways: the Contact Activation or thromboplastin-controlled pathway (formerly known as the extrinsic pathway) and the Tissue Factor or prothrombin/fibrinogen-controlled coagulation pathway (formerly known as the intrinsic pathway). Both the Contact Activation and Tissue Factor pathways result in the production of thrombin, a proteolytic enzyme which catalyzes the conversion of fibrinogen to fibrin.

Blood coagulation or clotting assays are principally used for screening or diagnosis and/or monitoring the hemostatic or coagulation status of a subject (e.g., a patient). There are many types of coagulation assays, including prothrombin time (PT), partial thromboplastin time (PTT) or activated partial thromboplastin time (APTT), fibrinogen assay, thrombin clotting time (TCT, TAT, or TT), activated clotting time (ACT). PT monitors the Contact Activation pathway of coagulation, and is useful for monitoring, e.g., antithrombotic therapy, for example, warfarin therapy. PTT or APTT detects factor changes in the Tissue Factor coagulation cascade (e.g., factors VIII, IX, XI, XII, other enzymes and factors), and is used primarily to monitor heparin therapy. Similarly, ACT evaluates the Tissue Factor pathways of coagulation and is useful for monitoring e.g., anticoagulation therapy, e.g., heparin therapy in situations where an APTT test cannot be performed, such as, for example if a patient was administered a high dose of heparin. TCT is not sensitive to deficiencies in either pathway, and measures a common pathway at the level of prothrombin to test for fibrinogen polymerization. The fibrinogen assay by the Clauss method (clotting method) utilizes activating levels of thrombin to initiate coagulation of a sample, and resulting coagulation time correlates with levels of fibrinogen in the sample.

The majority of coagulation assays for clinical assessment of patients are performed using the PT test. The PT test measures the activation of the Contact Activation coagulation pathway by addition of tissue thromboplastin. PT tests can be used for a number of different applications, including, for example, monitoring patients undergoing antithrombotic therapy (e.g., anticoagulant therapy) and assessing the status of a various clotting disorders including, e.g., acquired platelet function defect, congenital platelet function defects, congenital protein C or S deficiency, deep intracerebral hemorrhage, DIC (Disseminated intravascular coagulation), factor II deficiency, factor V deficiency, factor VII deficiency, factor X deficiency, hemolytic-uremic syndrome (HUS), hemophilia A, hemophilia B, hemorrhagic stroke, hepatic encephalopathy, hepatorenal syndrome; hypertensive intracerebral hemorrhage, idiopathic thrombocytopenic purpura (ITP), intracerebral hemorrhage, lobar intracerebral hemorrhage, placenta abruption, transient ischemic attack (TIA), and Wilson's disease.

Traditionally, coagulation parameters are determined by "wet chemistry" testing, wherein an aliquot of blood sample is mixed with one or more liquid coagulation reagents and the point of time at which the blood clots is detected. Results are indicated either directly (in seconds) or in the form of derived quantities such as ratio to a respective normal value (in percent). With respect to PT, common derived results for clotting indication include % Quick and the WHO standard, INR (International Normalized Ratio) values.

A number of various apparatuses and methods exist for measuring coagulation time of blood samples. Coagulation detection methods include detecting an increase in viscosity (viscosity detection method), detecting turbidity (turbidity detection method), and combined viscosity/turbidity detection methods. Other methods of coagulation detection employ multi-layered porous membranes impregnated with one or more coagulation reagents. Impregnated coagulation reagent(s) initiate coagulation of a sample (e.g., a predetermined blood volume), producing a detectable signal and the assays sometimes require predetermined blood volumes. Still other methods employ detection of oscillation of magnetic particles suspended in a reagent in a changing electric field, wherein oscillations change as a blood sample clots. Still other methods simply measure a change in light absorbance through a sample before and after a clotting reaction.

Most current methods have limitations which make them unsuitable or inconvenient for point of care testing or home use. Some require special blood sample preparation and handling or sophisticated equipment, making them suitable only for central laboratory facilities having qualified staff. Others, though possible for home use, are not cost effective for commercialization, or encounter implementation challenges (e.g., methods that require filtration of a sample through porous membranes pose wetting and uniform reagent impregnation difficulties).

Furthermore, besides cost and challenge of operation, a number of methods do not measure coagulation directly; and most tests do not measure coagulation without the use of an additive. Indirect measurement has been known to pose problems of accuracy in many samples. Other methods, while appearing to function well, can be limited to a narrow range of blood types, therapeutic windows, restricted by a long list of interfering factors or require large volumes of blood.

Thus, current blood coagulation tests are generally complex and the bulk of them are performed in a centralized clinical laboratory, at a clinic, or at a physician's office. Required visits to a clinic or a doctor's office on a regular basis to monitor anticoagulation therapy can be both inconvenient and expensive for a patient. Thus, there is a need for easy-to-use, compact, and portable instruments to facilitate use at "point of care" (POC) locations, within a surgical suite, or for a patient to monitor blood coagulation status at home.

SUMMARY OF THE INVENTION

The present invention provides non-optical methods for monitoring and measuring coagulation (e.g., blood coagulation, plasma coagulation) using nuclear magnetic resonance parameters detectable by relaxometer readings. Provided methods allow for accuracy and precision at point of care (POC) settings or at home settings, which are currently available only through central laboratory facilities. Provided methods can be used optionally without a need for additives beyond a coagulation reagent for initiating the coagulation process to be measured; can measure coagulation directly without sample interference due to non-invasive detection; allows fast determination of coagulation state changes, thereby providing real time monitoring of samples; are not limited to blood type, therapeutic window or other interfering factors; are not limited to clear samples required for optical assessment; require only small amounts of coagulating sample; and can provide highly time-resolved coagulation curves that allow for profiling of coagulation abnormalities. The present invention further provides test carriers for containing samples used in methods provided herein.

One embodiment of the present invention is a method for measuring a coagulation time. The method comprises providing a test carrier containing a sample within a detection volume of a NMR detector and measuring a change in a NMR parameter over time to determine the coagulation time, wherein the measured change in NMR parameter over time provides a measurement of coagulation time A further embodiment of the present invention is a method for determining the coagulation state and/or coagulation time of a sample using a nuclear magnetic resonance (NMR) device. The method includes the following steps: a) providing a test carrier containing the sample within a detection volume of an NMR detector of the NMR device; b) performing NMR measurements on the sample to determine at least two values of an NMR parameter of the sample over time, the NMR parameter being responsive to coagulation in the sample; and c) assessing the values determined in step b) to obtain the coagulation state and/or coagulation time of the sample.

A further embodiment of the present invention is a method for determining the extent of coagulation of a blood sample obtained from a subject. The method includes the following steps: a) measuring an NMR parameter of the blood sample, wherein the NMR parameter is responsive to the extent of coagulation; b) comparing the measured value of the NMR parameter obtained in step a) with a known value for the NMR parameter wherein the known value has been correlated with the extent of coagulation in blood; c) assessing the extent of coagulation from the comparison made in step b).

A further embodiment of the present invention is a method for determining the coagulation time of a blood sample obtained from a test subject. The method includes the following steps: a) measuring an NMR parameter of the blood sample, wherein the NMR parameter is responsive to the extent of coagulation; b) comparing the measured value of the NMR parameter at a given time obtained in step a) with a standard coagulation-time-curve that provides a standard curve of change of the NMR parameter over time due to coagulating blood; and c) determining the coagulation time from the comparison in step b).

A further embodiment of the present invention is a method for monitoring coagulation of a blood sample from a test subject. The method includes measuring a plurality of values of an NMR parameter of the blood sample over time, wherein the NMR parameter is responsive to the coagulation state of the blood sample.

A further embodiment of the present invention is a method for diagnosing an abnormal clotting event in a blood sample of a test subject. The method includes a) providing at least one test carrier, each test carrier containing a blood sample from the test subject, and being within a detection volume of an NMR detector; b) obtaining test data of an NMR parameter over time, the NMR parameter being responsive to coagulation in the blood sample of each test carrier; and c) comparing one or more characteristics of the test data obtained in step (b) with those of a standard coagulation-time-curve of the NMR parameter responsive to normal coagulation to thereby diagnose an abnormal clotting event in the subject.

A further embodiment of the present invention is a test carrier. In some embodiments a test carrier comprises a carrier and one or more coagulation reagents that induce or support coagulation in a sample. In other embodiments a test carrier comprises a carrier and one or more coagulation reagents that activate coagulation. In certain embodiments a test carrier includes a carrier in which one or more interior surfaces have been etched. In certain embodiments, a test carrier includes a carrier suitable for NMR measurements and one or more coagulation reagents that induce or support coagulation in a sample.

The foregoing will be apparent from the following more particular description of example embodiments with reference to the drawings described below, and the claims. The drawings are not necessarily to scale, emphasis instead generally being placed upon illustrating the principles of the invention. In the following detailed description, references are made to illustrative embodiments of methods and apparatus for carrying out the invention. It is understood that other embodiments can be utilized without departing from the scope of the invention. Preferred methods and apparatus are described for performing blood coagulation tests of the type described herein.

Throughout the description, where methods are described as having, including, or comprising steps, it is contemplated that, additionally, there are methods and systems of the present invention that consist essentially of or consist of, the recited processing steps. It should be understood that the order of steps or order for performing certain actions is immaterial so long as the invention remains operable. Moreover, two or more steps or actions may be conducted simultaneously.

DETAILED DESCRIPTION OF THE INVENTION

Figure 1:
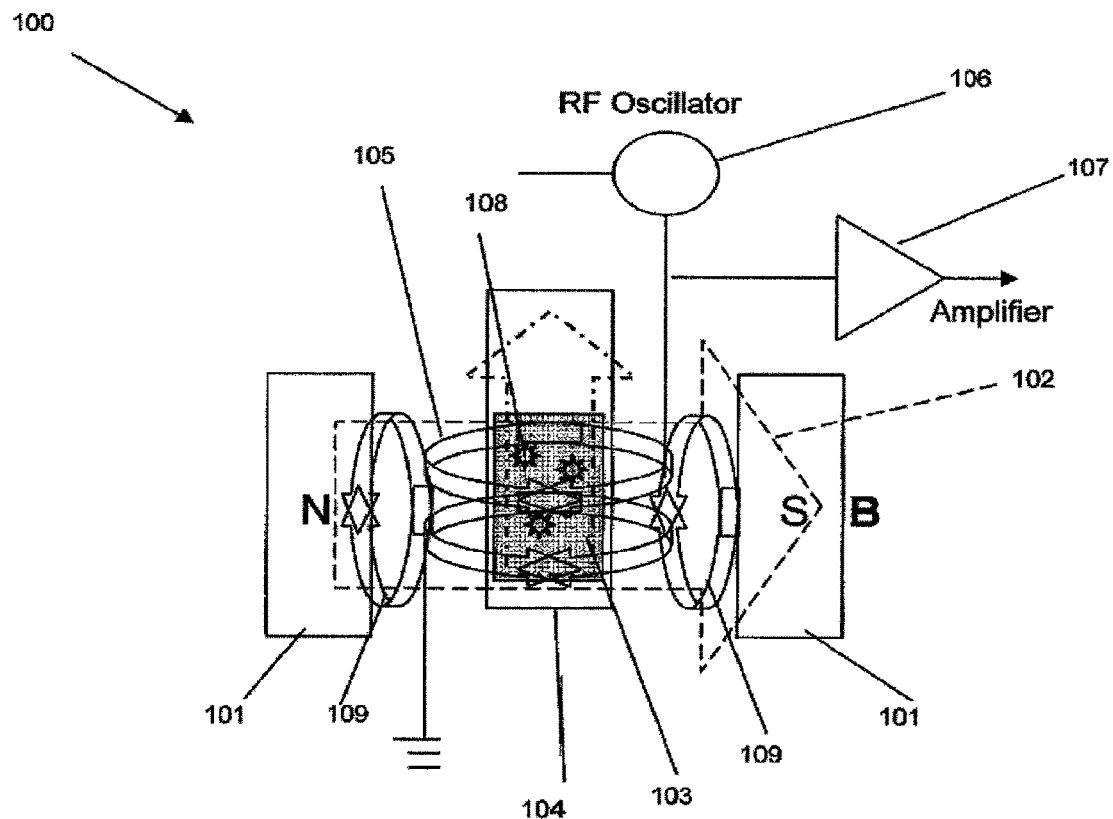
FIG. 1 depicts illustrative elements of an NMR detector and test carrier utilizing underlying principles of the present invention for measurement of coagulation time.

In a broad aspect, the present invention provides methods for detecting a change in a sample (e.g., a blood sample) coagulation state, for example, monitoring blood clotting (hereinafter also "coagulation") using time-resolved relaxation time acquisition methodology. Provided methods for measuring coagulation time of a sample (e.g., a blood sample) are simple to practice, rapid, and reliable.

As used herein, a "subject" encompasses mammals and non-mammals. Examples of mammals include, but are not limited to, any member of the mammalian class, including humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs; etc. Examples of non-mammals include, but are not limited to, birds, fish, etc. In some embodiments a subject includes a clinical patient.

As used herein, a sample can be a biologic sample, for example, a blood sample (e.g., whole blood, plasma, blood concentrate, citrated blood) from a subject, or a liquid containing compounds (e.g., monomers) that can coagulate, for example, upon providing conditions suitable for coagulation.

A blood sample can be obtained from a subject (e.g., a patient) by traditional means such as venipuncture or a finger prick. A sample can be applied, for example via sample application port, onto a test carrier. In one aspect of the invention, a sample of blood obtained from a subject can be used without additional manipulation in the methods and apparatus of the invention. In some embodiments a whole blood sample is used in conjunction with provided methods. Alternatively, a blood sample obtained from a subject can be treated to remove, either completely or partially, red blood cells. In some embodiments blood cells are removed by any of known methods, such as, for example, centrifugation, reacting sample with a red blood cell agglutinant, or by employing a red blood cell filter. In some embodiments plasma is used in conjunction with provided methods.

In some embodiments sample blood or plasma can be optionally diluted prior to coagulation. A diluent can simply be an aqueous solution or it can be a non-aqueous solution, and optionally can include various additives, such as, for example, salts, proteins, sugars, saccharides, metal ions, such as calcium, magnesium, lanthanides, and the like. Certain formulations of a diluent can include gelatin-containing composition and/or emulsion. In some embodiments, a diluent is a saline solution. In some embodiments, a diluent is a buffer solution, e.g., citrate buffer A sample may be maintained at a temperature of about 20° C. to about 40° C. In some embodiments a sample is maintained at about room temperature, about 22° C., about 25° C., about 30° C., about 35° C., about 37° C. or about 40° C. In certain embodiments, a blood sample is maintained at about body temperature, or about 37° C. Regardless of a preferred selected temperature, a sample is preferably maintained at about constant temperature throughout the process of obtaining measurement of NMR readings.

A coagulation time can be one or more of the blood coagulation times, including prothrombin time (PT), partial thromboplastin time (PTT), activated partial thromboplastin time (APTT), fibrinogen assay, thrombin clotting time (TCT), fibrinogen assay, and activated clotting time (ACT).

In certain embodiments a sample may be heparinized and/or mixed with one or more reagents. In some embodiments a reagent may include, for example, an anti-coagulant. In other embodiments, a reagent may include, for example, a coagulant, a coagulation agent (e.g., calcium (e.g., calcium chloride)), kaolin, celite, ellagic acid, glass particles, thrombin, thromboplastin, PT reagent, PTT or APTT reagent, ACT reagent, TCT reagent, fibrinogen reagent), or a heparin neutralizing or deactivating agent (e.g., heparinase, protamine).

As used herein, "coagulation reagent" refers to a reagent that induces and/or supports (e.g., accelerates) coagulation when mixed with the sample, for example, a blood sample, under conditions suitable for the reagent to induce or support coagulation in the sample. These conditions are known in the art. Coagulation reagents include but are not limited to a prothrombin time (PT) reagent, a partial thromboplastin time (PTT)/activated partial thromboplastin time (APTT) reagent, thrombin clotting time (TCT) reagent, fibrinogen reagent, an activated clotting time (ACT) reagent, calcium (e.g., calcium chloride)), kaolin, celite, ellagic acid, glass particles, thrombin, thromboplastin; wherein specific agents comprising reagents for each test(s) are well known and have been described in the art, and are available through commercially available sources.

For example, a PT reagent can include any of STA® Neoplastine CL, STA® Neoplastine CL Plus (Diagnostica Stago, Parsippany, N.J., USA); Thromborel S, Innovin, Thromboplastin CL, Thromboplastin C Plus (Dade Behring, Liederbach, GERMANY); Plastinex (BioData Corporation, Horsham, Pa., USA); Diaplastin (Diamed AG, SWITZERLAND); Thromboplastin, Thromboplastin M1 (Helena Laboratories, Beaufort, Tex., USA); PT-Fibrinogen, PT-Fibrinogen HS, PT-Fibrinogen HS+, PT-Fibrinogen Recombinant, Brain Thromboplastin, RecombiPlasTin (Instrumentation Laboratory, Bedford, Mass., USA); Simplastin, Simplastin Excel, Simplastin Excel 5, Simplastin L, MDA Simplastin L, Simplastin HTF, MDA Simplastin HTF (bioMerieux, St. Laurent, Quebec, CANADA); Thromboplastin-D with Calcium, Thromboplastin-DL with Calcium, Thromboplastin-DS, Thromboplastin Liquid (Pacific Hemostasis, Huntersville, N.C., USA); Thromboplastin with Calcium, Thromboplastin HS with Calcium, Thromboplastin M with Calcium, Thromboplastin XS with Calcium, ThromboMAX HS with calcium, ThromboMAX with calcium (Sigma Diagnostics, St. Louis, Mo., USA). An APTT/PTT reagent can include for example any of: Automated APTT Reagent, SILIMAT, Platelin®L, Platelin®LS, and MDA Platelin®L (bioMerieux, St. Laurent, Quebec, CANADA); Actin®, Actin®FS, Actin®FSL, and Pathromtin®SL (Dade Behring, Liederbach, GERMANY); APTT-SP, APTT-C, SynthASil, SynthAFax, and ThrombosIL (Instrumentation Laboratory, Bedford, Mass., USA); SPECTRA™ (Analytical Control Systems, Inc., Fishers, Ind., USA); Thrombosil, Activated Thrombofax (Ortho, Raritan, N.J., USA); CK-PREST, STA® PTT Automate (Diagnostica Stago, Parsippany, N.J., USA); Cephalinex® (BioData Corporation, Horsham, Pa., USA); APTT Reagent (Diamed AG, SWITZERLAND); APTT Reagent, APTT-FS, APTT-FSL, ALEXIN, ALEXIN HS, and ALEXIN LS (Sigma Diagnostics, St. Louis, Mo., USA). A fibrinogen reagent can include, for example, Fibri-Prest, STA®-Fibrinogen 5 (Diagnostica Stago, Parsippany, N.J., USA); Multifibren U, Fibrinogen Determination (Dade Behring Thrombin) (Dade Behring, Liederbach, GERMANY); Fibrinogen Assay (BioData Corporation, Horsham, Pa., USA); Fibrinogen Assay (Helena Laboratories, Beaufort, Tex., USA); QFA (bovine thrombin), Fibrinogen C, PT-Fibrinogen, PT-Fibrinogen HS, PT-Fibrinogen HS+, PT-Fibrinogen Recombinant, RecombiPlasTin. RecombiPlasTin4.5 (Instrumentation Laboratory, Bedford, Mass., USA); Fibriquik, Fibriquik (MDA Fibrinogen I-delta), Fibriquik (MDA Fibrinogen II-seconds) (bioMerieux, St. Laurent, Quebec, CANADA); Thromboscreen (Pacific Hemostasis, Huntersville, N.C., USA); Accuclot Fibrinogen (Sigma Diagnostics, St. Louis, Mo., USA). A TCT reagent can include, for example, any commercial or produced source of animal thrombin, e.g., STA®—Thrombin, Thrombin 10, (Diagnostica Stago, Parsippany, N.J., USA); Human alpha-Thrombin (Sigma Diagnostics, St. Louis, Mo., USA); MDA® Thromboquik, (bioMerieux, St. Laurent, Quebec, CANADA); BC-Thrombin reagent (Dade Behring, Liederbach, GERMANY). An ACT reagent can include, for example, any commercial or produced source of silica based coagulation activator compound, (e.g., kaolin, celite, ellagic acid, glass particles). Further, combinations of coagulation reagents can be used as reagents to induce and/or support coagulation.

As used herein, "carrier" is understood to mean any localizer of a liquid sample, for example, a well, an indentation, a support, a channel, a reservoir, a sunken volume, a compartment, a recessed area, an enclosure with or without an opening, a tube, or a trough. The term "test carrier" means a carrier into which a sample is deposited for analysis. A test carrier can be placed within the detection volume of an NMR detection coil, for example a relaxometer (i.e., Bruker Minispec) or a customized miniature relaxometer. A sample can be placed in the test carrier either before or after the test carrier is placed within the detection volume of a NMR detection coil. In certain embodiments, coagulation test time based on the measurement of viscosity of the sample using NMR relaxivity measurements can be ascertained under temperature control.

Figures 7A, 7B:
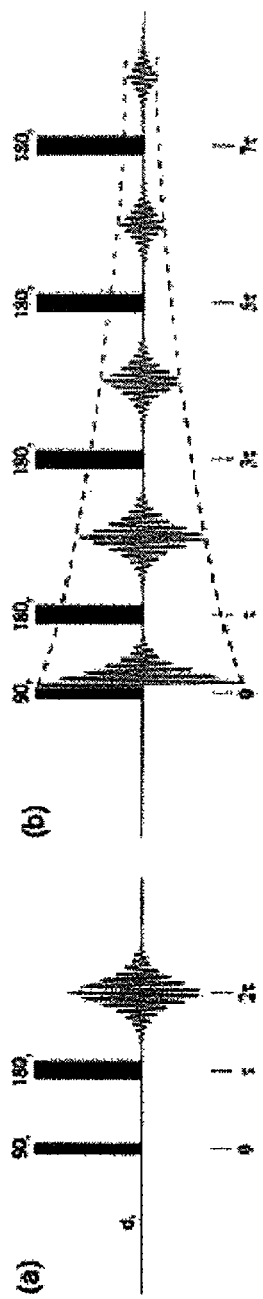
FIGS. 7a and 7b depict schematic graphical representations of two different magnetic resonance pulse sequences for measuring T$_2$: (7a) A spin echo sequence consists of two radiofrequency (RF) pulses: a 90°, x phase, and a 180°, y phase, separated by a delay τ. The echo signal appears at time 2τ. T$_2$ is measured by obtaining the echo signal from successive cycles using incremental values of τ. The recycle delay, d1, is typically 1-3 sec. (7b) A CPMG sequence allows for much faster T$_2$ measurements because multiple echos are acquired in rapid succession by a series of 180°, y phase RF pulses and signal acquisitions. T$_2$ measurements acquired with a CPMG sequence avoid diffusion artifacts because of the short time over which the measurement occurs.

It has been found that an effective $T_2$ relaxation rate (i.e. $1/T_2$) can be related to a coagulation state of a sample, and coagulation time can be determined by monitoring one or more parameters relating to a series of $T_2$ relaxation rate measurements over time (herein referred to as a coagulation-time-curve). Typically, in determining a coagulation time, a tailored radiofrequency (RF) pulse sequence is applied to a test carrier containing a sample; and RF echo signals are monitored and analyzed to determine one or more NMR parameters (e.g., $T_2$). For example, an effective $T_2$ relaxation rate as measured by a custom CPMG (Carr-Purcell-Meiboom-Gill) pulse sequence can be used to measure a temporal change in coagulation state. While true $T_2$ measurements with methods such as spin echos (see, e.g., FIG. 7a) can be obtained, such measurements do not typically yield the same sensitivity to coagulation state as methods provided herein, and thus are not useful in the current application. For example, to obtain a useful relaxation parameter for measuring a coagulation time with adequate temporal resolution (e.g. sampling rate), CPMG sequence parameters are adjusted such that obtained relaxation curves are sampled to obtain optimal coagulation response measurements, as described in further detail herein.

Suitable CPMG sequences for measuring effective $T_2$ of a sample can be characterized by the following sequence of steps: 1) waiting (i.e., not applying a radiofrequency pulse to a sample) at least for a time period given by a recycle delay (e.g., the time between initiation of a relaxation measurement and a first radiofrequency pulse, time between the end of prior sequence measurement to allow for the system to return to equilibrium (e.g., about 0.5 to about 5 seconds); 2) applying a 90° radiofrequency pulse to the sample, 3) waiting for a time period given by, for example, one-half the inter-echo delay, 4) applying a 180° radiofrequency pulse to the sample, 5) waiting for a time period given by the inter-echo delay, and optionally, repeating steps 4) and 5) one or more times. See, e.g., FIG. 7b. In certain embodiments a relaxation measurement optionally coincides with one or more of completion of a previous pulse sequence measurement, insertion of a sample into the magnet, etc. In particular embodiments initiation of a relaxation measurement coincides with completion of a previous relaxation measurement pulse sequence. Following application of each 180° radiofrequency pulse, a sample responds with an echo that can be acquired to determine $T_2$ by methods known in the art. See, e.g., Carr, H. Y., and Purcell, E. M., "Effects of Diffusion on Free Procession in Nuclear Magnetic Resonance Experiments," Phy. Rev. 904, No. 3:630 (1954); Meiboom, S.; and Gill, D., "Modified Spin-Echo Method for Measuring Nuclear Relaxation Times," Rev. Sci. Inst. 29 (1958), which are hereby incorporated by reference; and, described, e.g., U.S. Pat. Nos. 6,690,166, 5,023,551. With increasing repetitions of steps 4) and 5), echos become weaker, leading to a practical limit of how many echos can be recorded with a single CPMG sequence using a given device and given measurement conditions/settings. In certain embodiments all echos within the practical limit of detectable echos are recorded. In other embodiments less than all echos within the practical limit of detectable echos in a single CPMG sequence are recorded. For example, spectrometer recording hardware may constrain the total number of echos that can be recorded. In this case, for example, a subset of detectable echos are recorded, (e.g., acquiring one of every four echos (e.g., herein referred to as a CPMG sequence characterized by a dummy echo value of three)). In some embodiments more than one CPMG sequence is employed, e.g., more than one measurement of $T_2$ is performed per sample. When more than one measurement of $T_2$ is performed per sample, each of the CPMG sequence(s) are separated in time by a recycle delay.

In the case of blood coagulation that is expected to be characterized by blood coagulation times on the order of several minutes and/or if low time resolution of the blood coagulation curve is required, parameters characterizing a custom CPMG sequence can be determined using methods known in the art, because the time between $T_2$ value measurements is large compared to the signal decay time used to determine $T_2$. Typically, blood coagulation times are short and/or higher time resolution is preferred. For example, for $T_2$ values of larger than 1.5 seconds and $T_1$ values larger than 1.5 seconds, upon first approximation, a dwell time (that is, acquisition time plus recycle delay) of about 5 seconds would appear to be needed to measure true sequential $T_2$ values. Accordingly, for very short blood coagulation times, for example, of about ~10 seconds, one would expect to only be able to obtain one, or at most two of measurements of true $T_2$ prior to coagulation. Generally, it is desired to measure the time course of coagulation with as high as possible time resolution. Higher time resolution typically means higher accuracy of parameters characterizing coagulation, for example, coagulation times and better comparison between coagulation curves, for example, comparison of a patient's blood/plasma coagulation curve with a standard curve for normal blood/plasma coagulation (see, e.g., Example 3).

It has now been found that the parameters of a CPMG sequence can be optimized to allow determination of "effective" $T_2$ values (note, the term "$T_2$" as used herein, if not specifically denoted as "effective" refers to both "true" and "effective" $T_2$) that yield high sensitivity to reflect changes in coagulation state while providing adequate temporal resolution, or dwell time (e.g. the time between $T_2$ measurements must be short enough to provide a kinetic trace throughout the coagulation process). This optimization allows for sensitive measurements over the time course of the coagulation process, thus generating a series of $T_2$ measurements, which provide a metric by which coagulation time is determined. The measured $T_2$ value is actually an effective $T_2$ because the $T_2$ value is influenced by the optimization of the CPMG sequence, that is, the "true" $T_2$ requires acquisitions times that are not amenable to a short dwell times; therefore effective $T_2$ measurements are required. To optimize CPMG sequence measurements, parameters are changed to: 1) maximize the change in $T_2$ measurements over the coagulation process (maximize overall delta $T_2$); 2) minimize noise levels of measurements taken (e.g., particularly at the upper and lower $T_2$ measurement extremes); and to increase the number of $T_2$ measurements taken over time in order to provide adequate sample measurements over the time course of coagulation so as to generate a useful coagulation wave form. Using the principles described herein in conjunction with knowledge in the art, one skilled in the art could modify parameters described herein in various combinations to achieve the results taught in the present methods. In addition or alternatively, with the provided description, one skilled in the art may modify parameters that may vary slightly from the provided ranges, and/or in conjunction with other parameters in a CPMG sequence, or other sequential relaxation signal measurements, to similarly optimize relaxation measurement sequence(s) to obtain coagulation measurements as provided herein.

In some embodiments, a recycle delay is between 0.1 seconds and 100 seconds. In particular embodiments, a recycle delay is between 0.5 seconds and 1 second. In certain embodiments, a recycle delay is about 1 second.

In some embodiments, an inter-echo delay is between 0.01 milliseconds and 10 milliseconds. In particular embodiments, an inter-echo delay is between 0.2 milliseconds and 2 milliseconds. In certain embodiments, an inter-echo delay is about 0.5 milliseconds.

In some embodiments, the number of acquired echos is between 1 and 10,000. In particular embodiments, the number of acquired echos is between 500 and 2,000. In certain embodiments, the number of acquired echos is between 1500 and 2000.

In some embodiments, the number of dummy echos is between 0 and 50. In particular embodiments, the number of dummy echos is between 0 and 10. In certain embodiments, the number of dummy echos is between 0 and 3.

Acquisition time is known in the art, and, in particular with regard to CPMG pulse sequence measurements, is the interecho delay time times the number of acquired echoes, times the sum of one plus the number of dummy echoes in a sequence: at=[ied*ae*(1+de)]. In some embodiments, an acquisition time is between 0.01 milliseconds and 5,100 seconds. In particular embodiments, an acquisition time is between 0.1 and 44 seconds. In certain embodiments, an acquisition time is between about 0.5 and about 8 seconds. In particular embodiments, an acquisition time is about 3.5 seconds or about 4.5 seconds.

Dwell time is known in the art, and, in particular with regard to CPMG pulse sequence measurements, is the length of a recycle delay plus the length of acquisition time of a sequence: dt=[rd+at]. In some embodiments, a dwell time is between 0.1 seconds and about 5,200 seconds. In particular embodiments, a dwell time is between 0.6 and 45 seconds. In certain embodiments, a dwell time is between about 1 second and about 6 seconds. In particular embodiments a dwell time is about 4.5 or about 5.5 seconds.

In some embodiments a dwell time is sufficient to allow for taking at least two $T_2$ values while sample is coagulating and before the sample is coagulated. In some embodiments a dwell time is sufficient to allow for taking at least five $T_2$ values while a sample is coagulating and before the sample is coagulated. In certain embodiments a dwell time is sufficient to allow for taking at least ten $T_2$ values while a sample is coagulating and before the sample is coagulated.

In an embodiment of the present invention, a recycle delay is between 0.1 and 100 seconds, the number of acquired echos is between 1 and 10,000, the number of dummy echos is between 0 and 50, an inter-echo delay is between 0.01 and 10 milliseconds, and the number of $T_2$ measurements (i.e., number of sequential CPMG sequences) is between 2 and 10,000, leading to acquisition times between 0.00001 seconds and 5,100 seconds and dwell times between 0.1 second and 5,200 seconds.

In a further embodiment of the present invention, a recycle delay is between 0.5 and 1 seconds, the number of acquired echos is between 500 and 2,000, the number of dummy echos is between 0 and 10, an inter-echo delay is between 0.2 and 2 milliseconds, and the number of $T_2$ measurements (i.e., number of sequential CPMG sequences) is between 100 and 500, leading to acquisition times between 0.1 and 44 seconds and dwell times between 0.6 and 45 seconds.

In a preferred embodiment of the present invention, a recycle delay is between about 0.8 and about 1 second, the number of acquired echos is between about 1650 and about 1850, the number of dummy echos is between 0 and 5, and an inter-echo delay is between about 0.3 and about 0.7 msleading to acquisition times between about 0.5 and about 7.8 seconds and dwell times between about 1.3 and about 8.8 seconds.

In a further preferred embodiment of the present invention, a recycle delay is about 1 second, the number of acquired echos is about 1,750, the number of dummy echos is about 3, and an inter-echo delay is about 0.5 milliseconds, leading to an acquisition time of about 3.5 seconds and a dwell time of about 4.5 seconds.

Determination of coagulation times using methods of the present invention is based on the measurement of a nuclear magnetic parameter, typically $T_2$, over time. In some embodiments, one measurement of $T_2$ of a coagulating sample at a time before the sample is substantially fully coagulated can be sufficient to determine the extent of coagulation and/or a coagulation time. For example, if a $T_2$ value has been determined for a normally coagulating sample, the $T_2$ value and corresponding time can be matched (e.g., by visual inspection, computationally, etc.) to a pre-determined standard coagulation-time-curve for the type of coagulating sample. If a standard coagulation-time-curve has been correlated with the extent of coagulation for the type of coagulating sample (i.e., the extent of coagulation for given $T_2$ values at given times on the standard coagulation-time-curve has been determined), a single $T_2$ measurement can provide the extent of coagulation. Further, comparison of a $T_2$ value and corresponding time with a standard coagulation-time-curve can allow determination of a sample coagulation time or determination of an estimate of the sample coagulation time. For example, if a measured $T_2$ value at a given time point matches a $T_2$ value of the standard curve for the given time point, the sample coagulation time could be associated with the standard coagulation-time-curve.

In some embodiments, a plurality of $T_2$ values over time are determined using methods of the present invention to assess coagulation, for example, to determine coagulation state (i.e., not coagulated or coagulated), the extent of coagulation (e.g., percentage coagulation), and/or a coagulation time (e.g., prothrombin time (PT), partial thromboplastin time (PTT), activated partial thromboplastin time (APTT), thrombin clotting time (TCT), fibrinogen assay clotting time, activated clotting time (ACT)).

Typically, for determination of a coagulation time of a plasma or whole blood sample, the start time for coagulation is the timepoint when coagulation is initiated in the sample, for example, by mixing a coagulation activating reagent (e.g., calcium) with a sample. A plurality of $T_2$ values are measured before the sample is substantially fully coagulated, and, typically, further one or more $T_2$ values are determined for the substantially fully coagulated sample. A resulting coagulation time curve provided by the measured $T_2$ values over time allows for a determination of the coagulation time. As can be seen for normal and abnormal plasma coagulation curves in FIGS. 2 to 6, coagulation typically leads to a decline of the measured $T_2$ values from a top plateau to a bottom plateau. See Exemplification and FIGS. 2 to 6. A coagulation time can be determined based on a measured coagulation time curve alone, by comparison with a standard coagulation-time-curve, and/or by normalizing with a pre-determined calibration factor.

For example, based on an obtained coagulation time curve alone, coagulation time can be determined as the time from coagulation initiation, for example, using a coagulation reagent, to the time point that the bottom plateau is reached.

A preferred way of determining a coagulation time from measured $T_2$ values is to average, independently, $T_2$ values of a top plateau to obtain a top plateau value $T_{2,t}$ and $T_2$ values of a bottom plateau to obtain a bottom plateau value $T_{2,b}$ and determine the time for which $T_2$ is at the value $T_{2,b}+(T_{2,t}-T_{2,b})/2$ on the coagulation time curve, and normalizing the obtained time with a pre-determined calibration factor. This determination also provides a midpoint value between the initial (top plateau) $T_2$ and the final (bottom plateau) $T_2$ on a $T_2$ plasma coagulation curve. See, e.g., FIGS. 2 to 6.

In some embodiments a difference between a first average $T_2$ value (e.g., of a top plateau) and a second average $T_2$ value (e.g., of a bottom plateau) is substantially larger than the average standard error of a $T_2$ measurement using a CPMG sequence. In some embodiments a difference between a first average $T_2$ value (e.g., of a top plateau) and a second average $T_2$ value (e.g., of a bottom plateau) is at least 3% of the first $T_2$ value. In some embodiments a difference between a first average $T_2$ value (e.g., of a top plateau) and a second average $T_2$ value (e.g., of a bottom plateau) is at least 5% of the first $T_2$ value. In certain embodiments a difference between a first average $T_2$ value (e.g., of a top plateau) and a second average $T_2$ value (e.g., of a bottom plateau) is at least 10% of the first $T_2$ value. In particular embodiments a difference between a first average $T_2$ value (e.g., of a top plateau) and a second average $T_2$ value (e.g., of a bottom plateau) is at least 13% of the first $T_2$ value.

A calibration factor can be determined by determining the time as described above for one or more samples and determining for the same samples a coagulation time using a commercially available method for determining coagulation (e.g., the Start®4 method using the Diagnostica Stago device), and determining the factor by which the times determined using the methods of the present invention have to be multiplied with to obtain the coagulation times determined by the commercially available method. In this case, a data point given by the $T_2$ value and the corresponding time of $T_2$ measurement is matched a standard coagulation-time-curve is required to which the determined $T_2$ value can be compared.

As used herein, a "standard coagulation-time-curve" refers to data correlating values of an NMR parameter responsive to coagulation of a sample (e.g., a blood sample, a plasma sample, a fraction of blood in a sample) of one or more subjects, or values mathematically derived from values obtained over time. Data can be, but is not limited to be, in the form of a curve. Graphical presentation of obtained data in terms of a scatter or line plot/graph, for example, with an NMR parameter on the ordinate and time on the abscissa can provide an easy way to compare measured values of an NMR parameter with a corresponding standard coagulation-time-curve. Further, a sample used in determination of a "standard coagulation-time-curve" is taken from one or more subjects that exhibit normal coagulation processes and timing of coagulation processes. The one or more subjects from which samples are used for generation of a standard coagulation time curve can differ but don't have to differ from a test subject for which coagulation is or will be assessed using methods of the present invention. For example, a standard coagulation time curve may be generated using samples obtained from normal healthy patients, and a sample that will be measured and compared to the generated standard coagulation time curve is obtained from a patient requiring assessment of anticoagulant therapy. The sample from the patient is not part of the pool of samples used to generate the standard coagulation time curve. In another example, a standard coagulation-time-curve may be generated using sample(s) of blood of a test subject (e.g., a patient) prior to a procedure or therapy (e.g., a surgery that requires post-surgical administration of an anticoagulant). Coagulation of blood of the patient may be assessed from samples obtained from the patient while the patient is receiving anticoagulant using methods of the present invention and comparing obtained results to a subject's standard coagulation-time-curve determined prior to surgery. In some embodiments one or more standard coagulation time curves are prepared independently in advance and provided as a standard control curve for individual testing of samples for any one or more coagulation times (e.g., prothrombin time (PT), partial thromboplastin time (PTT), activated partial thromboplastin time (APTT), thrombin clotting time (TCT), fibrinogen assa clotting time, activated clotting time (ACT)). In certain embodiments one or more standard coagulation time curves are prepared and provided as part of instructions and reference materials as part of a coagulation test kit. In some embodiments, one or more standard coagulation curves are prepared in advance (e.g., immediately prior to) or in conjunction with (e.g., in parallel) an individual sample preparation and testing. In certain embodiments one or more standard coagulation curves are prepared initially upon first use of a lot of provided reagents, wherein the prepared standard coagulation curve(s) are used for comparison to one or more test sample coagulation curves, and continually used for each of those test samples which utilize the same lot of reagents for sample coagulation tests.

A coagulation time can be determined by monitoring elapsed time corresponding to one or more parameters of a coagulation-time-curve including a predetermined magnitude change in the coagulation-time-curve, a percent change from baseline of the magnitude of the coagulation-time-curve, the first derivative of the coagulation-time-curve, the second derivative of the coagulation time curve, higher derivatives of the coagulation-time-curve, to an inflection point, to a steady-state value, and combinations thereof. Parameters can be monitored as a magnitude of elapsed time or as a function of time to enable a calculation or derivation of a characteristic value or characteristic kinetic rate (i.e. half-life of the signal, etc.). If desired, a characteristic value or rate can be compared to a standard or control relating to one or more parameters of a coagulation state of a sample, either simultaneously or sequentially. A standard can take many specific forms, but may be generically described as a data set relating the characteristic value or rate to a coagulation time determined by a standard coagulation instrument (e.g. calibration curve).

In some embodiments of the invention, a sample can be mixed with a coagulation reagent before being placed in the test carrier or can interact with a reagent coated on the surfaces of the test carrier. Additionally or alternatively, a sample may be mixed with a coagulation reagent disposed in the test carrier, either before or after a sample is placed in the test carrier. For example, surfaces of a test carrier may be coated with the coagulation reagent or a discrete element that is coated with or includes a coagulation reagent is disposed in the test carrier prior to, at the same time as, or after addition of a sample.

Moreover, a test carrier walls can be surface-etched to increase surface area and to enhance surface roughness that can cause fibrin to develop in a sample (e.g., a blood sample (e.g., whole blood, plasma, etc.). Surface roughness may activate or facilitate coagulation of a sample, either in place of or in addition to a coagulation reagent. A test carrier can be a fabrication of any natural, synthetic, porous, non-porous, non-metallic, magnetic susceptibility matched, hydrophobic or hydrophilic material (e.g., plastic (i.e. Delrin or Teflon), glass, Mylar). Furthermore, a test carrier may be of any geometric shape capable of isolating, or accommodating, or absorbing, or containing a volume of solution including capillaries, tubes, hollow channels, conduits, microfluidics, porous membranes, and encapsulations. For example, the carrier may be a glass capillary or tube used for NMR relaxation measurements. A test carrier may accommodate volume samples in the range of 1 picoliter to 1 milliliter, preferably microliters, more preferably 1 to 500 microliters, most preferably 10 to 300 microliters.

The present invention also provides methods for monitoring (for example, in real-time) coagulation of a blood sample of a test subject that makes use of measurements of an NMR parameter over time. Comparing obtained values for a monitored NMR parameter with a standard coagulation-time-curve provides information regarding abnormal coagulation events.

Monitoring blood coagulation over time provides a clotting profile of a sample and provides information concerning discrete normal or abnormal events that may accompany the coagulation, clotting or lytic process (e.g., clot formation, clot retraction, or clot lysis), as well as providing insight into the overall event. The present invention is useful in distinguishing between platelet-rich and platelet-poor plasma depending on the clotting profile of a sample.

The present invention also provides methods for diagnosing an abnormal clotting event in a test subject. At least one test carrier is provided, wherein each test carrier contains a sample (e.g., a blood sample) from a test subject and is placed within a detection volume of a NMR detector. Test data of a NMR parameter responsive to coagulation in the sample of each test carrier is obtained over time, for example, by measuring values of the NMR parameter over time. One or more characteristics of the test data are compared with those of a standard coagulation-time-curve in the NMR parameter responsive to normal coagulation to identify and thereby diagnose an abnormal clotting event in the subject (see, for example, FIG. 3 and FIG. 4). Any suitable characteristic associated with the test data can be compared. Examples include overall change of the NMR parameter over time, rate of the NMR parameter change over time, clotting time determined from the NMR parameter change, and fluctuation of the NMR parameter change in the sample prior to coagulation. Preferably, the test data of the NMR parameter are obtained by monitoring values of the NMR parameter over time to provide a coagulation (clotting) profile of the sample.

In one specific embodiment of methods of the invention, a plurality of samples (e.g., blood samples) from a test subject are collected at discrete times. In one example, a first test carrier and a second test carrier contain a first sample and a second sample from the same test subject, but collected at discrete times. Difference(s) between the first and second samples in coagulation can be obtained by comparing characteristic(s) of the obtained test NMR data (e.g., clotting profile) between the first and second samples. With such comparison, for example, one can determine if any change is present from (e.g., a first abnormal clotting event diagnosed from a first blood sample over the time period between the first and second blood collection). In another specific embodiment, a first and a second sample are collected from different test subjects. In this example, difference(s) between the first and second samples in coagulation (e.g., clotting profile) can provide information to distinguish between discrete abnormal clotting events relative to the standard coagulation-time-curve (see, for example, FIG. 5).

The present methods are also useful for providing information concerning discrete events that may accompany the coagulation, clotting or lytic process (e.g., clot formation, clot retraction, or clot lysis), as well as providing insight into the overall event. Provided methods can be useful in distinguishing between platelet-rich and platelet-poor plasma depending on the clotting profile of the sample. The methods can also provide information useful to physicians developing a treatment plan for patients during and following surgery including cardiopulmonary bypass surgery to avoid or mitigate pre-operative, perioperative, and/or post-operative bleeding.

A brief summary of the technical elements relating to the principles of the present invention is provided herein. The underlying principle of the present invention for coagulation state measurement and its use in determining coagulation time is based on the assumption of single-exponential decay functions obtained from NMR radiofrequency (RF) echo signals. According to this model for coagulation state determination, an effective $T_2$ relaxivity change over time is related to a sample coagulation state and inversely proportional to temperature. Provided methods allow measurement of the kinetics of coagulation by monitoring changes in relaxation times. For example, in certain embodiments, measurements (e.g., 10-20 measurements) can be made after mixing a sample and a reagent to initiate coagulation, before coagulation is complete, and coagulation times can be determined from the resulting kinetic curves.

In FIG. 1, an NMR system is depicted to illustrate the principle on which the invention is explained on the basis of several embodiments. The depiction is not intended to limit the invention to a particular embodiment, but serves for the purpose of explaining the illustrative elements of devices utilizing the underlying principles for the measurement of one or more NMR parameter(s) to provide a sample coagulation time.

FIG. 1 is a schematic diagram 100 of an NMR system for detection of an echo response of a sample 103 to an RF excitation, thereby determining the coagulation state of the sample and a corresponding coagulation time. In a specific embodiment, a sample 103 within test carrier 104 is placed within the sensitive region of an RF coil 105 of device 100. Device 100 comprises bias magnets 101 that generate a bias magnetic field $B_0$ 102 through a sample 103. An RF excitation pulse at the Larmor frequency is applied to a sample using RF coil 105 and RF oscillator 106. The RF excitation and subsequent series of 180 degree pulses induces what is known in the art as a CPMG echo train. Amplitude of these echos decays as a function of time, which is known as a $T_2$ relaxation curve. The coil 105 can be configured to act synchronously as an RF antenna to detect the echo signal. RF signal obtained from a coil 105 is amplified by amplifier 107 and processed to determine a change in the relaxation curve in response to the excitation applied to the sample 103. The detected and processed signal is preferably the $T_2$ relaxation time. A series of $T_2$ relaxation times is monitored over a period of time from an initial set of values to a steady set of values. A corresponding coagulation time of the sample can be calculated using a standard data set or a calibration curve for comparison with the series of monitored $T_2$ relaxation times.

In alternative embodiments, various configurations of carrier 104 may be used for coagulation time testing. Other configurations of the bias magnetic field $B_0$ 102 can be applied to sample 103 including, unilateral magnetic fields, low powered magnetic fields, and the earth's magnetic field.

In one embodiment, an RF coil 105 is wrapped around the sample carrier 104. In alternative embodiments, RF coil 105 can be a planar RF coil or other shape and form of RF coil can be used with sample carrier 104.

In certain embodiments, alternative and/or additional reagents can be added to a sample carrier 104 prior or introduced simultaneously with a sample 103 into carrier 104. Gradient coils 109 can be used to apply discrete, intermittent, or continuous magnetic gradient forces on sample 103, coagulation reagent 108, and optional additional and/or alternative regents. For example, $T_2$ relaxivity measurements of a sample can be taken independent of coagulation measurements described herein to assess viscosity of a sample using magnetic particles. See, e.g., WO2009/026164, the disclosure of which is incorporated herein by reference. Additionally or alternatively, $T_2$ relaxation rates may be analyzed to ascertain the mechanical integrity of clot formation within a sample over a period of time particularly to identify coagulopathic characteristics of a blood sample.

In some embodiments, a coagulation time test is conducted on one or more samples that are "incubated" in a test carrier 104 (e.g., incubating in a test chamber) by maintaining samples at a preferred temperature (e.g., body temperature) for a defined incubation time period. For example, in certain embodiments it may be necessary to incubate sample (e.g., citrated whole blood, plasma, or quality control sample(s)) prior to running measurements (e.g., for ACT test(s)). Blood sample(s) drawn from a patient and immediately placed within the test carrier 104 before the sample has cooled may not need an incubation period and may only need to be maintained at 37° C. Thus, a heating element (e.g., a heat block (not shown)) can be incorporated within device 100 in relation to a carrier 104. Preferably a heating element (e.g., a heat block) is continuously powered when device 100 is powered in order to maintain a constant temperature (e.g., body temperature, 37° C.) to a test carrier 104 inserted into the RF coil 105.

In certain embodiments, a suitable reagent 108 may be selected to react with a sample (e.g., a blood sample) to facilitate sample coagulation (e.g., for performance of a particular test on a blood sample for determining sample coagulation times, e.g., one of PT, aPTT, TT, and ACT). In some embodiments a suitable reagent 108 may be added to a sample carrier 104 prior or introduced simultaneously with sample 103 into carrier 104. In some embodiments a coagulation reagent 108 can be included in a sample carrier 104 prior wherein when an added sample 103 is place in carrier 104, sample reacts with the reagent 108. In particular embodiments coagulation reagent(s) may be selected from coagulants or activating agents including calcium, kaolin, celite, ellagic acid, glass particles, thrombin, thromboplastin or other coagulation agents described herein and known in the art. In some embodiments, coagulation reagents are selected from one or more coagulating agents selected from a prothrombin time (PT) reagent, a partial thromboplastin time (PTT)/activated partial thromboplastin time (APTT) reagent, thrombin clotting time (TCT) reagent, fibrinogen reagent, an activated clotting time (ACT) reagent, calcium (e.g., calcium chloride)), kaolin, celite, ellagic acid, glass particles, thrombin, and/or thromboplastin.

In other embodiments, test carrier 104 may also contain or optionally accommodate additional reagent(s). In some embodiments to counteract any anticoagulant(s) present in a blood sample. For example, during interventional procedures, heparin may be administered to a subject to mitigate coagulation induced by a procedure, in which case neutralizing or deactivating agent(s) (e.g., heparinase, protamine) in test carrier 104 could counteract heparin and return the blood sample to a baseline condition. For example, one test carrier 104 could contain protamine, and another test carrier 104 could be devoid of protamine to perform comparative coagulation time tests.

EXAMPLE 1

Coagulation Time Measurement in Plasma Using $T_2$ Relaxation

A Bruker Minispec mQseries (The Woodlands, Tex.) was adapted with pulse sequences for $T_2$ monitoring in real time. Several effective $T_2$ measurements made within 30 to 40 seconds and transverse relaxation times of plasma samples were measured every 5 seconds. Coagulation of a sample was induced by addition of calcium chloride to a mixture of reconstituted plasma (CITREX® I lyophilized plasma preparation, BIODATA Corporation, Horsham, Pa·S) and an aPTT reagent (CEPHALINEX® activated partial thromboplastin time reagent BIODATA Corporation, Horsham, Pa., USA).

$T_2$ measurements were made kinetically on a Bruker MQ minispec using preloaded minispec software with the following CPMG settings:
1. Tau=0.25
2. Number of Points=1000
3. Dummy Echos: 3
4. Recycle Delay: 1
5. 0 dB pulse at 37° C.
6. Receiver gain: 75
7. 1 scan Coagulation time was estimated by curve analysis completed by midpoint determination between the $T_2$ initial and $T_2$ final. See FIG. 2. During coagulation, the relaxation time of the plasma sample decreased steadily until the sample was fully coagulated. See FIG. 2. The overall change in $T_2$ observed was about 300 ms.

Figure 2:
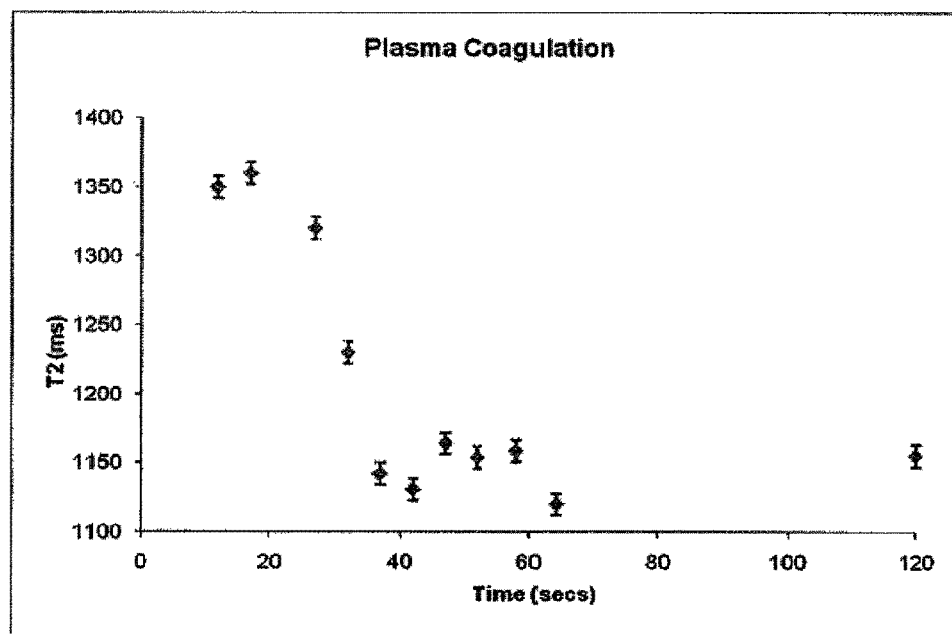
FIG. 2 depicts a graphical result demonstrating reduction in T$_2$ relaxation time during coagulation induced by addition of calcium chloride to a mixture of plasma and an APTT reagent, CEPHALINEX®.
Figure 3:
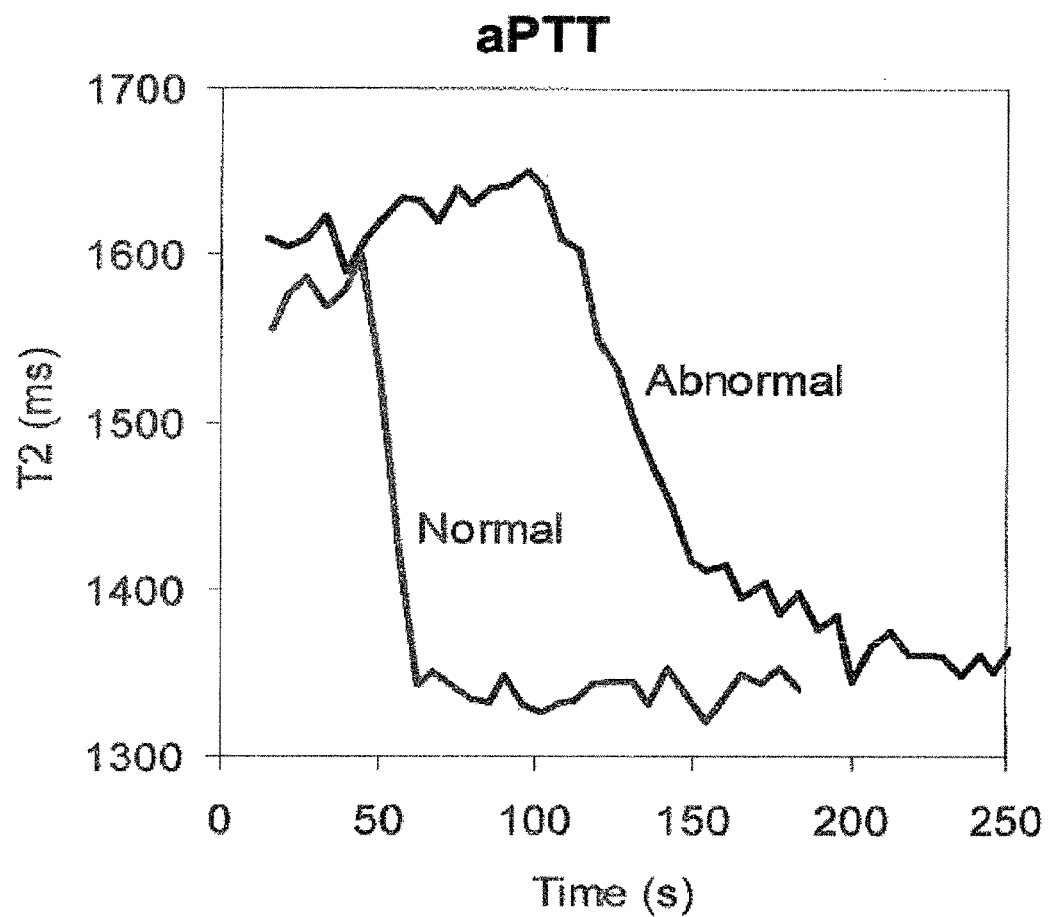
FIG. 3 depicts a graphical result providing normal and abnormal aPTT plasma clotting/coagulation obtained by measuring changes of T$_2$ relaxation time over time using time-resolved relaxation time acquisition methodology.
Figure 4:
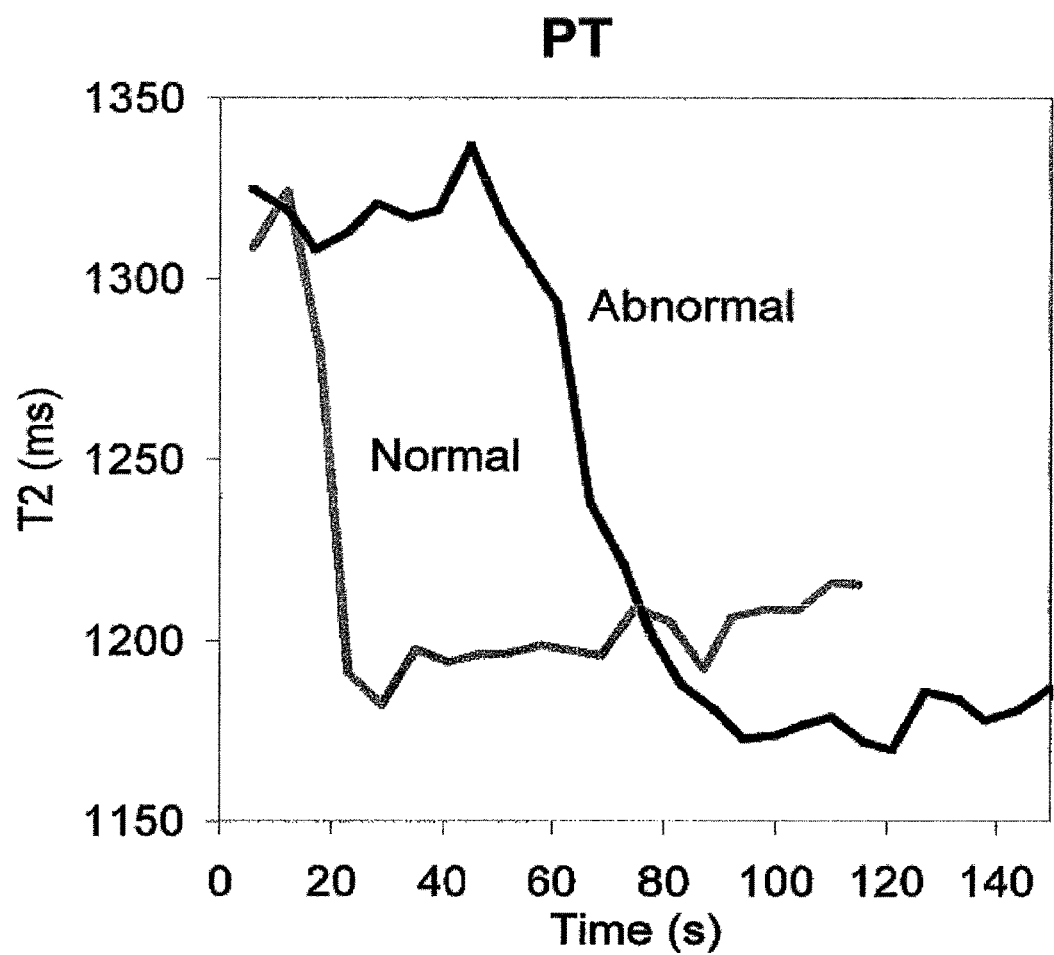
FIG. 4 depicts a graphical result providing normal and abnormal PT plasma clotting/coagulation obtained by measuring changes of T$_2$ relaxation time over time using time-resolved relaxation time acquisition methodology.

Coagulation time was determined to be about 35s based on the curve in FIG. 2.

EXAMPLE 2

Coagulation Measurements Using Pooled Normal and Single Donor Abnormal Samples via $T_2$ Relaxation Real patient plasmas were purchased through George King Bio-Medical and used within 2 hours following thawing. Both normal and abnormal samples were run in duplicate to provide experimental error (averages are shown). Duplicate sampling resulted in a more precise coagulation time compared to the reference (start-4) data. (Note: standard deviation of samples controlled two factors: effective $T_2$ values, coagulation time).

Measurement of changes in $T_2$ relaxation time over time were taken. Measurements were made kinetically on a Broker MQ minispec using preloaded minispec software with the following CPMG settings:

1. Tau=0.25
2. Number of Points=1750
3. Dummy Echos: 3
4. Recycle Delay: 1
5. 18 dB pulse at 37° C.
6. Receiver gain: 75
7. 1 scan Curve analysis was completed to generate coagulation times by midpoint determination between the $T_2$ initial and $T_2$ final.

Figure 5:
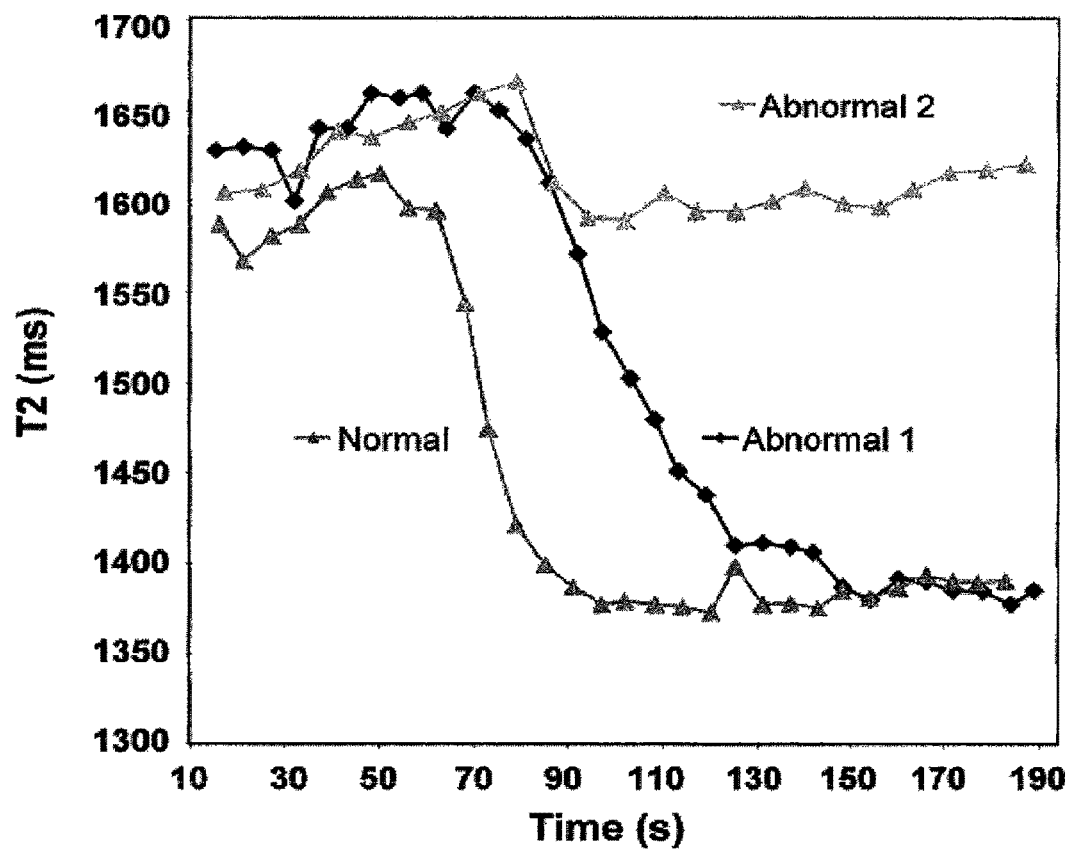
FIG. 5 depicts a graphical result providing two discrete abnormal plasma clotting/coagulation curves, relative to normal plasma clotting/coagulation, obtained by measuring changes of T$_2$ relaxation time over time using time-resolved relaxation time acquisition methodology.

2A. For aPTT coagulation measurements 100 μL of patient plasma and 100 μL of aPTT clotting reagent PTT-A (Diagnostica Stago, Parsippany, N.J.) were pre-warmed to 37° C. in a 5 mm NMR tube. 100 μL of calcium chloride pre-warmed to 37° C. was added to the plasma and clotting reagent activating coagulation. See, FIG. 3 and FIG. 5. The overall change in $T_2$ observed was about 250 ms for the normal sample, and about 250 ms for the abnormal sample. Coagulation time was determined to be about 50 sec for the normal sample, and about 140 sec for the abnormal sample based on the curve in FIG. 3. In FIG. 5, overall change in $T_2$ observed was about 205 ms for the normal sample, 300 ms for abnormal sample 1, and about 95 ms for abnormal sample 2. Coagulation time was determined to be about 70 sec for the normal sample, and about 100 sec for the abnormal sample and about 90 sec for abnormal sample 2 based on the curve in FIG. 5.

2B. For PT coagulation measurements 100 μL of patient plasma and 200 μL of Neoplastine CI Plus (Diagnostica Stago, Parsippany, N.J.) pre-warmed to 37° C. were mixed activating coagulation. See FIG. 4. The overall change in $T_2$ observed was about 150 ms for the normal sample, and about 160 ms for the abnormal sample. Coagulation time was determined to be about 19 sec for the normal sample, and about 67 sec for the abnormal sample based on the curve in FIG. 4.

EXAMPLE 3

Correlation Between Coagulation Method Results Obtained Using a Method of the Present Invention and Results Obtained with a Commercial Bench-top Coagulation Instrument For aPTT measurements, 100 μL of patient plasma and 100 μL of PTT-A (Diagnostica Stago) were pre-warmed to 37° C. in a 5 mm NMR tube. 100 μL of calcium chloride pre-warmed to 37° C. was added to the plasma and clotting reagent activating coagulation. For PT measurements 100 μL of patient plasma and 200 μL of Neoplastine CI Plus (Stago Diagnostica, Parsippany, N.J.) pre-warmed to 37° C. were mixed activating coagulation. Measurements were made kinetically on a Bruker MQ minispec using preloaded minispec software with CPMG parameters described in Example 2. Curve analysis to generate coagulation times was completed by midpoint determination between the $T_2$ initial and $T_2$ final.

Figure 6:
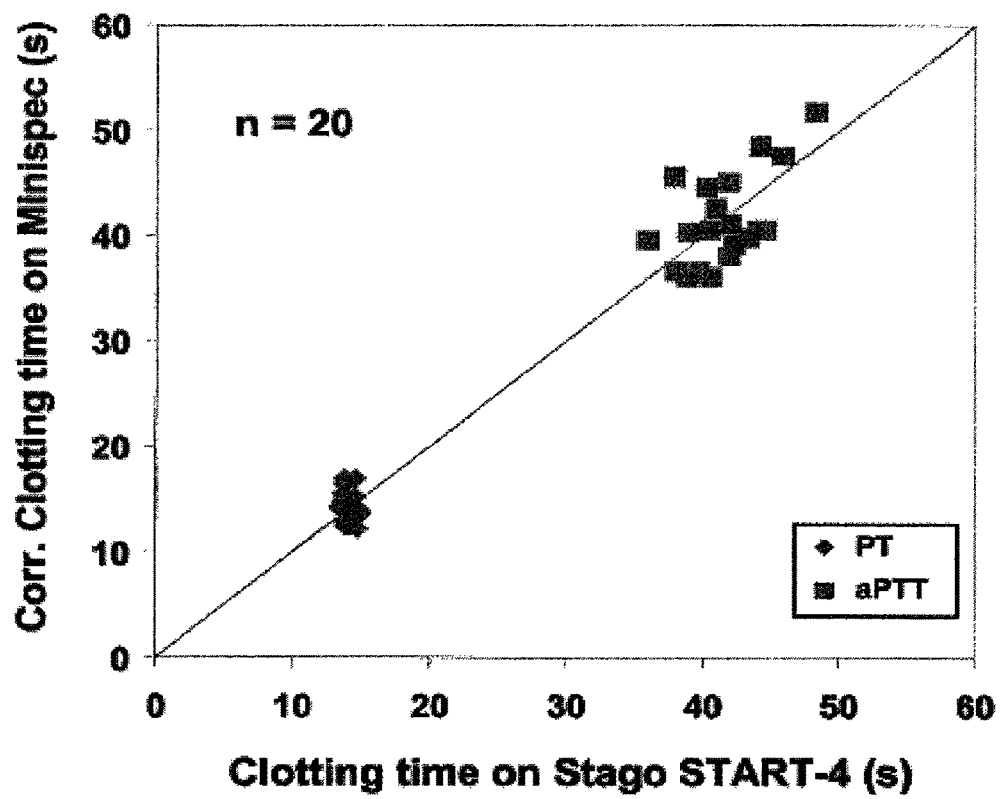
FIG. 6 depicts a graphical result providing a correlation between a coagulation measurement method of the present invention and a commercial bench-top coagulation instrument from Diagnostica Stago (Parsippany, N.J.), called the Start-4. Prothrombin Time (PT) and Activated Partial Thromboplastin Time (aPPT) were measured with both methods.

Prothrombin Time (PT) and Activated Partial Thromboplastin Time (aPPT) of plasma samples were measured using a Bruker Minispec mQseries and a commercial bench-top coagulation instrument from Diagnostica Stago (Parsippany, N.J.), called the Start®4. FIG. 6 shows a correlation plot representing a graphical comparison of these two methods. As is known in the art, a subtraction factor was applied to time measured by T2 Biosystems to provide a correlation with the Diagnostica Stago Start®4. This subtraction factor was determined by subtracting a fixed value which resulted in all normal coagulation values derived with the NMR instrument to be in a clinically normal range. The correlation data points are very close to the plot diagonal, indicating excellent correlation of the results obtained using two very different approaches for measuring coagulation times.

While this invention has been particularly shown and described with references to example embodiments thereof, it will be understood by those skilled in the art that various changes in form and details may be made therein without departing from the scope of the invention encompassed by the appended claims.

The invention claimed is:

1. A method of determining the coagulation time of a blood sample obtained from a subject, comprising:
   (a) providing a blood sample from a subject;
   (b) placing the blood sample in a carrier;
   (c) mixing a coagulation reagent with said blood sample to initiate coagulation;
   (d) measuring a $T_2$ relaxation time of the blood sample in the carrier within a detection volume of an NMR detector of an NMR device using a CPMG sequence until the blood sample is substantially fully coagulated, wherein in a coagulation-time-curve (i) an uncoagulated state is characterized by a first plateau in the coagulation-time-curve, the first plateau having a first average $T_2$ value, and (ii) a coagulated state is characterized by a second plateau in the coagulation-time-curve, the second plateau having a second average $T_2$ value, and wherein the CPMG sequence is characterized by parameters that permit detection of at least two values of the $T_2$ of the sample within about 10 seconds of performing step (c); and
   (e) based upon the coagulation-time-curve determining the coagulation time of the sample.

2. The method of claim 1, wherein the difference between the first average $T_2$ value and the second average $T_2$ value is at least 3%.

3. The method of claim 1, wherein step (e) further comprises assessing the extent of coagulation in the sample based upon the decline in $T_2$ measured once the blood sample is substantially fully coagulated.

4. The method of claim 1, wherein the coagulation reagent is a prothrombin time coagulation reagent.

5. The method of claim 1, wherein the coagulation reagent is an activated partial thromboplastin time coagulation reagent.

6. The method of claim 1, wherein the coagulation reagent is a partial thromboplastin time coagulation reagent.

7. The method of claim 1, wherein the coagulation reagent is a thrombin clotting time coagulation reagent.

8. The method of claim 1, wherein the coagulation reagent is a fibrinogen reagent.

9. The method of claim 1, wherein the carrier is incubated to maintain the blood sample at a preferred temperature prior to step (c).

10. The method of claim 1, wherein the carrier is placed in a heating block prior to step (c).

11. The method of claim 1, wherein the volume of the blood sample is from 10 to 300 microliters.

12. The method of claim 1, wherein the carrier comprises a surface fabricated from plastic.

13. The method of claim 1, wherein the blood sample is a whole blood sample.

14. The method of claim 1, wherein the blood sample is a plasma sample.

15. The method of claim 1, wherein the CPMG sequence is characterized by an inter-echo delay of between 0.2 milliseconds and 2 milliseconds and a dwell time of between about 1 second and about 6 seconds.

16. The method of claim 15, wherein the CPMG sequence is characterized by a recycle delay of about 1 second.

17. The method of claim 15, wherein the CPMG sequence is characterized by a number of acquired echoes of between 500 and 2,000.

18. The method of claim 15, wherein the CPMG sequence is characterized by an inter-echo delay of about 0.5 milliseconds.

19. The method of claim 15, wherein the CPMG sequence is characterized by a dwell time of about 4.5 or about 5.5 seconds.

* * * * *